United States Patent
Miraki et al.

(10) Patent No.: US 10,470,759 B2
(45) Date of Patent: Nov. 12, 2019

(54) SUTURE SECUREMENT DEVICES

(71) Applicant: Edwards Lifesciences Corporation, Irvine, CA (US)

(72) Inventors: Manouchehr A. Miraki, Laguna Hills, CA (US); Hengchu Cao, Irvine, CA (US); Ralph Schneider, Trabuco Canyon, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 599 days.

(21) Appl. No.: 15/064,006

(22) Filed: Mar. 8, 2016

(65) Prior Publication Data

US 2016/0270776 A1 Sep. 22, 2016

Related U.S. Application Data

(60) Provisional application No. 62/133,810, filed on Mar. 16, 2015.

(51) Int. Cl.
*A61B 17/04* (2006.01)

(52) U.S. Cl.
CPC .. *A61B 17/0487* (2013.01); *A61B 2017/0404* (2013.01); *A61B 2017/0438* (2013.01); *A61B 2017/0454* (2013.01)

(58) Field of Classification Search
CPC .... A61B 2017/0404; A61B 2017/0414; A61B 17/0487; Y10T 24/44991; Y10T 24/44923;
(Continued)

(56) References Cited

U.S. PATENT DOCUMENTS

| 1,358,477 A | 11/1920 | Stout |
| 2,264,679 A | 12/1941 | Ravel |

(Continued)

FOREIGN PATENT DOCUMENTS

| CA | 2141911 A1 | 8/1995 |
| CA | 2141913 A1 | 8/1995 |

(Continued)

OTHER PUBLICATIONS

International Search Report for PCT/US2014/046423, dated Oct. 20, 2014.
(Continued)

*Primary Examiner* — Thomas M McEvoy
(74) *Attorney, Agent, or Firm* — Klarquist Sparkman, LLP

(57) ABSTRACT

Some disclosed suture securement devices comprise a flat, thin, generally planar body that has one or more suture engagement slots extending into the body from a perimeter inlet for receiving sutures laterally into the device. The slots can be resiliently widened to receive a suture and then released to clamp onto the suture. Some embodiments include two or more such suture engagement slots that independently receive and secure different sutures. Some embodiments include one or more locking tabs that have a closed position that retains the slots against widening and blocks the inlet to the slot. In some embodiment two or more slots are position next to each other on the same side of the device, while in other embodiments slots are positioned on opposite sides of the device. Other types of suture securement devices are also disclosed.

20 Claims, 8 Drawing Sheets

(58) Field of Classification Search
CPC . Y10T 24/155; Y10T 24/205; Y10T 24/4465; Y10T 24/44752; Y10T 24/44744; Y10T 24/3918
See application file for complete search history.

(56) References Cited

U.S. PATENT DOCUMENTS

| | | |
|---|---|---|
| 2,516,710 A | 7/1950 | Mascolo |
| 2,715,486 A | 8/1955 | Marcoff-Moghadam et al. |
| 2,890,519 A | 6/1959 | Storz, Jr. |
| 2,981,990 A | 5/1961 | Balderree, Jr. |
| 3,143,742 A | 8/1964 | Cromie |
| 3,249,104 A | 5/1966 | Hohnstein |
| 3,274,658 A | 9/1966 | Pile |
| 3,452,742 A | 7/1969 | Muller |
| 3,506,012 A | 4/1970 | Brown |
| 3,509,882 A | 5/1970 | Blake |
| 3,541,591 A | 11/1970 | Hoegerman |
| 3,547,103 A | 12/1970 | Cook |
| 3,570,497 A | 3/1971 | Lemole |
| 3,608,095 A | 9/1971 | Barry |
| 3,638,654 A | 2/1972 | Akuba |
| RE27,391 E | 6/1972 | Merser |
| 3,753,438 A | 8/1973 | Wood et al. |
| 3,859,668 A | 1/1975 | Anderson |
| 3,875,648 A | 4/1975 | Bone |
| 3,898,999 A | 8/1975 | Haller |
| 3,910,281 A | 10/1975 | Kletschka et al. |
| 3,954,108 A | 5/1976 | Davis |
| 3,954,109 A | 5/1976 | Patel |
| 3,958,576 A | 5/1976 | Komiya |
| 3,976,079 A | 8/1976 | Samuels et al. |
| 3,988,810 A | 11/1976 | Emery |
| 3,996,623 A | 12/1976 | Kaster |
| 4,038,725 A | 8/1977 | Keefe |
| 4,103,690 A | 8/1978 | Harris |
| 4,140,125 A | 2/1979 | Smith |
| 4,170,990 A | 10/1979 | Baumgart et al. |
| 4,192,315 A | 3/1980 | Hilzinger et al. |
| 4,217,902 A | 8/1980 | March |
| 4,324,248 A | 4/1982 | Perlin |
| 4,345,601 A | 8/1982 | Fukuda |
| 4,416,266 A | 11/1983 | Baucom |
| 4,456,017 A | 6/1984 | Miles |
| 4,485,816 A | 12/1984 | Krumme |
| 4,522,207 A | 6/1985 | Klieman et al. |
| 4,535,764 A | 8/1985 | Ebert |
| 4,548,202 A | 10/1985 | Duncan |
| 4,549,545 A | 10/1985 | Levy |
| 4,570,304 A | 2/1986 | Montreuil et al. |
| 4,586,502 A | 5/1986 | Bedi et al. |
| 4,586,503 A | 5/1986 | Kirsch et al. |
| 4,595,007 A | 6/1986 | Mericle |
| 4,612,932 A | 9/1986 | Caspar et al. |
| 4,637,380 A | 1/1987 | Orejola |
| 4,665,906 A | 5/1987 | Jervis |
| 4,683,895 A | 8/1987 | Pohndorf |
| 4,705,040 A | 11/1987 | Mueller et al. |
| 4,719,924 A | 1/1988 | Crittenden et al. |
| 4,730,615 A | 3/1988 | Sutherland et al. |
| 4,741,330 A | 5/1988 | Hayhurst |
| 4,743,253 A | 5/1988 | Magladry |
| 4,750,492 A | 6/1988 | Jacobs |
| 4,809,695 A | 3/1989 | Gwathmey et al. |
| 4,823,794 A | 4/1989 | Pierce |
| 4,863,460 A | 9/1989 | Magladry |
| 4,873,975 A | 10/1989 | Walsh et al. |
| 4,896,668 A | 1/1990 | Popoff et al. |
| 4,899,744 A | 2/1990 | Fujitsuka et al. |
| 4,901,721 A | 2/1990 | Hakki |
| 4,914,789 A | 4/1990 | Pedersen |
| 4,924,866 A | 5/1990 | Yoon |
| 4,926,860 A | 5/1990 | Stice et al. |
| 4,929,240 A | 5/1990 | Kirsch et al. |
| 4,932,955 A | 6/1990 | Merz et al. |
| 4,950,283 A | 8/1990 | Dzubow et al. |
| 4,950,285 A | 8/1990 | Wilk |
| 4,955,913 A | 9/1990 | Robinson |
| 4,976,715 A | 12/1990 | Bays et al. |
| 4,983,176 A | 1/1991 | Cushman et al. |
| 4,990,152 A | 2/1991 | Yoon |
| 4,997,439 A | 3/1991 | Chen |
| 5,002,550 A | 3/1991 | Li |
| 5,002,562 A | 3/1991 | Oberlander |
| 5,002,563 A | 3/1991 | Pyka et al. |
| 5,026,379 A | 6/1991 | Yoon |
| 5,047,047 A | 9/1991 | Yoon |
| 5,053,047 A | 10/1991 | Yoon |
| 5,070,805 A | 12/1991 | Plante |
| 5,071,431 A | 12/1991 | Sauter et al. |
| 5,074,874 A | 12/1991 | Yoon et al. |
| 5,078,731 A | 1/1992 | Hayhurst |
| 5,100,418 A | 3/1992 | Yoon et al. |
| 5,116,840 A | 5/1992 | Ganguly et al. |
| 5,123,913 A | 6/1992 | Wilk et al. |
| RE34,021 E | 8/1992 | Mueller et al. |
| 5,152,769 A | 10/1992 | Baber |
| 5,154,189 A | 10/1992 | Oberlander |
| 5,158,566 A | 10/1992 | Pianetti |
| 5,163,954 A | 11/1992 | Curcio et al. |
| 5,171,250 A | 12/1992 | Yoon |
| 5,171,251 A | 12/1992 | Bregen et al. |
| 5,171,252 A | 12/1992 | Friedland |
| 5,174,087 A | 12/1992 | Bruno |
| 5,196,022 A | 3/1993 | Bilweis |
| 5,219,358 A | 6/1993 | Bendel et al. |
| 5,222,976 A | 6/1993 | Yoon |
| 5,231,735 A | 8/1993 | Paxton |
| 5,234,449 A | 8/1993 | Bruker et al. |
| 5,236,440 A * | 8/1993 | Hlavacek .......... A61B 17/0644 227/902 |
| 5,242,456 A | 9/1993 | Nash et al. |
| 5,246,443 A | 9/1993 | Mai |
| 5,258,011 A | 11/1993 | Drews |
| 5,258,015 A | 11/1993 | Li et al. |
| 5,269,783 A | 12/1993 | Sander |
| 5,269,809 A | 12/1993 | Hayhurst et al. |
| 5,282,832 A | 2/1994 | Toso et al. |
| 5,290,289 A | 3/1994 | Sanders et al. |
| 5,304,204 A | 4/1994 | Bregen |
| 5,306,290 A | 4/1994 | Martins et al. |
| 5,306,296 A | 4/1994 | Wright et al. |
| 5,312,423 A | 5/1994 | Rosenbluth et al. |
| 5,312,436 A | 5/1994 | Coffey et al. |
| 5,330,442 A | 7/1994 | Green et al. |
| 5,330,503 A | 7/1994 | Yoon |
| 5,336,239 A | 8/1994 | Gimpelson |
| 5,356,424 A | 10/1994 | Buzerak et al. |
| 5,374,268 A | 12/1994 | Sander |
| 5,381,588 A | 1/1995 | Nelson |
| 5,383,904 A | 1/1995 | Totakura et al. |
| 5,383,905 A | 1/1995 | Golds et al. |
| 5,391,173 A | 2/1995 | Wilk |
| 5,403,346 A | 4/1995 | Loeser |
| 5,409,499 A | 4/1995 | Yi |
| 5,437,680 A | 8/1995 | Yoon |
| 5,437,685 A | 8/1995 | Blasnik |
| 5,439,479 A | 8/1995 | Shichman et al. |
| 5,445,167 A | 8/1995 | Yoon et al. |
| 5,450,860 A | 9/1995 | O'Connor |
| 5,452,733 A | 9/1995 | Sterman et al. |
| 5,456,246 A | 10/1995 | Schmieding et al. |
| 5,462,561 A | 10/1995 | Voda |
| 5,474,557 A | 12/1995 | Mai |
| 5,474,572 A | 12/1995 | Hayhurst |
| 5,480,405 A | 1/1996 | Yoon |
| 5,486,197 A | 1/1996 | Le et al. |
| 5,496,336 A | 3/1996 | Cosgrove et al. |
| 5,499,990 A | 3/1996 | Schulken et al. |
| 5,500,000 A | 3/1996 | Feagin et al. |
| 5,520,691 A | 5/1996 | Branch |
| 5,520,702 A | 5/1996 | Sauer et al. |
| 5,527,342 A | 6/1996 | Pietrzak et al. |
| 5,531,763 A | 7/1996 | Mastri et al. |

(56) References Cited

U.S. PATENT DOCUMENTS

| | | |
|---|---|---|
| 5,545,178 A | 8/1996 | Kensey et al. |
| 5,549,619 A | 8/1996 | Peters et al. |
| 5,562,685 A | 10/1996 | Mollenauer et al. |
| 5,569,274 A | 10/1996 | Rapacki et al. |
| 5,569,301 A | 10/1996 | Granger et al. |
| 5,573,543 A | 11/1996 | Akopov et al. |
| 5,582,616 A | 12/1996 | Bolduc et al. |
| 5,582,619 A | 12/1996 | Ken |
| 5,586,983 A | 12/1996 | Sanders et al. |
| 5,591,179 A | 1/1997 | Edelstein |
| 5,593,414 A | 1/1997 | Shipp et al. |
| 5,593,424 A | 1/1997 | Northrup, III |
| 5,609,608 A | 3/1997 | Benett et al. |
| 5,626,590 A | 5/1997 | Wilk |
| 5,630,824 A | 5/1997 | Hart |
| 5,632,752 A | 5/1997 | Buelna |
| 5,632,753 A | 5/1997 | Loeser |
| 5,643,289 A | 7/1997 | Sauer et al. |
| 5,643,295 A | 7/1997 | Yoon |
| 5,645,553 A | 7/1997 | Kolesa et al. |
| 5,645,568 A | 7/1997 | Chervitz et al. |
| 5,665,109 A | 9/1997 | Yoon |
| 5,669,917 A | 9/1997 | Sauer et al. |
| 5,669,935 A | 9/1997 | Rosenman et al. |
| 5,681,351 A | 10/1997 | Jamiolkowski et al. |
| 5,683,417 A | 11/1997 | Cooper |
| 5,695,505 A | 12/1997 | Yoon |
| 5,697,943 A | 12/1997 | Sauer et al. |
| 5,700,270 A | 12/1997 | Peyser et al. |
| 5,700,271 A | 12/1997 | Whitfield et al. |
| 5,707,380 A | 1/1998 | Hinchliffe et al. |
| 5,709,693 A | 1/1998 | Taylor |
| 5,709,695 A | 1/1998 | Northrup, III |
| 5,725,539 A | 3/1998 | Matern |
| 5,725,542 A | 3/1998 | Yoon |
| 5,725,556 A | 3/1998 | Moser et al. |
| 5,728,135 A | 3/1998 | Bregen et al. |
| 5,735,290 A | 4/1998 | Sterman et al. |
| 5,735,877 A | 4/1998 | Pagedas |
| 5,766,183 A | 6/1998 | Sauer |
| 5,776,188 A | 7/1998 | Shepherd et al. |
| 5,799,661 A | 9/1998 | Boyd et al. |
| 5,810,851 A | 9/1998 | Yoon |
| 5,810,882 A | 9/1998 | Bolduc et al. |
| 5,820,631 A | 10/1998 | Nobles |
| 5,824,008 A | 10/1998 | Bolduc et al. |
| 5,830,221 A | 11/1998 | Stein et al. |
| 5,833,696 A | 11/1998 | Whitfield et al. |
| 5,845,645 A | 12/1998 | Bonutti |
| 5,849,019 A | 12/1998 | Yoon |
| 5,852,851 A | 12/1998 | Cooper |
| 5,861,004 A | 1/1999 | Kensey et al. |
| 5,879,371 A | 3/1999 | Gardiner et al. |
| 5,891,130 A | 4/1999 | Palermo et al. |
| 5,891,160 A | 4/1999 | Williamson, IV et al. |
| 5,895,393 A | 4/1999 | Pagedas |
| 5,895,394 A | 4/1999 | Kienzle et al. |
| 5,919,207 A | 7/1999 | Taheri |
| 5,948,001 A | 9/1999 | Larsen |
| 5,961,481 A | 10/1999 | Sterman et al. |
| 5,961,539 A | 10/1999 | Northrup, III et al. |
| 5,964,772 A | 10/1999 | Bolduc et al. |
| 5,972,024 A | 10/1999 | Northrup, III et al. |
| 5,976,159 A | 11/1999 | Bolduc et al. |
| 5,984,917 A | 11/1999 | Fleischman et al. |
| 5,989,242 A | 11/1999 | Saadat et al. |
| 5,989,268 A | 11/1999 | Pugsley, Jr. et al. |
| 5,997,556 A | 12/1999 | Tanner |
| 6,001,110 A | 12/1999 | Adams |
| 6,013,084 A | 1/2000 | Ken et al. |
| 6,015,428 A | 1/2000 | Pagedas |
| 6,039,176 A | 3/2000 | Wright |
| 6,066,160 A | 5/2000 | Colvin et al. |
| 6,074,409 A | 6/2000 | Goldfarb |
| 6,120,524 A | 9/2000 | Taheri |
| 6,132,438 A | 10/2000 | Fleischman et al. |
| 6,139,540 A | 10/2000 | Rost et al. |
| 6,143,004 A | 11/2000 | Davis et al. |
| 6,176,413 B1 | 1/2001 | Heck et al. |
| 6,190,373 B1 | 2/2001 | Palermo et al. |
| 6,193,733 B1 | 2/2001 | Adams |
| 6,193,734 B1 | 2/2001 | Bolduc et al. |
| 6,231,592 B1 | 5/2001 | Bonutti et al. |
| 6,241,765 B1 | 6/2001 | Griffin et al. |
| 6,254,615 B1 | 7/2001 | Bolduc et al. |
| 6,306,141 B1 | 10/2001 | Jervis |
| 6,346,112 B2 | 2/2002 | Adams |
| 6,368,334 B1 | 4/2002 | Sauer |
| 6,432,123 B2 | 8/2002 | Schwartz et al. |
| 6,475,230 B1 | 11/2002 | Bonutti et al. |
| 6,514,265 B2 | 2/2003 | Ho et al. |
| 6,533,796 B1 | 3/2003 | Sauer et al. |
| 6,537,290 B2 | 3/2003 | Adams et al. |
| 6,551,332 B1 | 4/2003 | Nguyen et al. |
| 6,589,279 B1 | 7/2003 | Anderson et al. |
| 6,607,541 B1 | 8/2003 | Gardiner et al. |
| 6,613,059 B2 | 9/2003 | Schaller et al. |
| 6,626,930 B1 | 9/2003 | Allen et al. |
| 6,641,592 B1 | 11/2003 | Sauer et al. |
| 6,641,593 B1 | 11/2003 | Schaller et al. |
| 6,682,540 B1 | 1/2004 | Sancoff et al. |
| 6,719,767 B1 | 4/2004 | Kimblad |
| 6,746,457 B2 | 6/2004 | Dana et al. |
| 6,749,622 B2 | 6/2004 | McGuckin, Jr. et al. |
| 6,776,784 B2 | 8/2004 | Ginn |
| 6,860,890 B2 | 3/2005 | Bachman et al. |
| 6,896,686 B2 | 5/2005 | Weber |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,945,980 B2 | 9/2005 | Nguyen et al. |
| 6,960,221 B2 | 11/2005 | Ho et al. |
| 7,011,669 B2 | 3/2006 | Kimblad |
| 7,083,628 B2 | 8/2006 | Bachman |
| 7,094,244 B2 | 8/2006 | Schreck |
| 7,112,207 B2 | 9/2006 | Allen et al. |
| 7,220,266 B2 | 5/2007 | Gambale |
| 7,235,086 B2 | 6/2007 | Sauer et al. |
| 7,264,625 B1 | 9/2007 | Buncke |
| 7,381,210 B2 | 6/2008 | Zarbatany et al. |
| 7,628,797 B2 | 12/2009 | Tieu et al. |
| 7,677,525 B2 | 3/2010 | Sanchez et al. |
| 7,731,727 B2 | 6/2010 | Sauer |
| 7,833,237 B2 | 11/2010 | Sauer |
| 7,842,051 B2 | 11/2010 | Dana et al. |
| 7,862,548 B2 | 1/2011 | Javer et al. |
| 7,862,584 B2 | 1/2011 | Lyons et al. |
| 7,875,056 B2 | 1/2011 | Jervis et al. |
| 7,959,674 B2 | 6/2011 | Shu et al. |
| 7,981,139 B2 | 7/2011 | Martin et al. |
| 8,021,421 B2 | 9/2011 | Fogarty et al. |
| 8,100,923 B2 | 1/2012 | Paraschac et al. |
| 8,105,355 B2 | 1/2012 | Page et al. |
| 8,252,005 B2 | 8/2012 | Findlay, III et al. |
| 8,398,657 B2 | 3/2013 | Sauer |
| 8,398,680 B2 | 3/2013 | Sauer et al. |
| 8,425,555 B2 | 4/2013 | Page et al. |
| 8,465,505 B2 | 6/2013 | Murillo et al. |
| 8,480,686 B2 | 7/2013 | Bakos et al. |
| 8,753,373 B2 | 6/2014 | Chau et al. |
| 9,017,347 B2 | 4/2015 | Oba et al. |
| 2001/0025181 A1 | 9/2001 | Freedlan |
| 2002/0029060 A1 | 3/2002 | Hogendijk |
| 2003/0009196 A1 | 1/2003 | Peterson |
| 2003/0093091 A1 | 5/2003 | Paolitto et al. |
| 2003/0109922 A1 | 6/2003 | Peterson et al. |
| 2003/0195563 A1 | 10/2003 | Foerster |
| 2003/0233105 A1 | 12/2003 | Gayton |
| 2004/0181238 A1 | 9/2004 | Zarbatany et al. |
| 2004/0204724 A1 | 10/2004 | Kissel et al. |
| 2004/0249414 A1 | 12/2004 | Kissel et al. |
| 2005/0217198 A1* | 10/2005 | Carraher ............ E04C 5/163 52/719 |

(56) References Cited

U.S. PATENT DOCUMENTS

| | | |
|---|---|---|
| 2005/0251206 A1 | 11/2005 | Maahs et al. |
| 2005/0251209 A1 | 11/2005 | Saadat et al. |
| 2006/0047314 A1 | 3/2006 | Green |
| 2006/0079913 A1 | 4/2006 | Whitfield et al. |
| 2006/0089571 A1 | 4/2006 | Gertner |
| 2006/0184203 A1 | 8/2006 | Martin et al. |
| 2006/0265010 A1 | 11/2006 | Paraschac et al. |
| 2006/0276871 A1 | 12/2006 | Lamson et al. |
| 2006/0282119 A1 | 12/2006 | Perchik |
| 2007/0005079 A1 | 1/2007 | Zarbatany et al. |
| 2007/0005081 A1 | 1/2007 | Findlay et al. |
| 2007/0049952 A1 | 3/2007 | Weiss |
| 2007/0049970 A1 | 3/2007 | Belef et al. |
| 2007/0088391 A1 | 4/2007 | McAlexander et al. |
| 2007/0157438 A1* | 7/2007 | Judd ............... B65H 75/36 24/115 R |
| 2007/0179530 A1 | 8/2007 | Tieu et al. |
| 2007/0255296 A1 | 11/2007 | Sauer |
| 2007/0270907 A1 | 11/2007 | Stokes et al. |
| 2008/0077144 A1* | 3/2008 | Crofford ............ A61B 17/064 606/75 |
| 2008/0154286 A1 | 6/2008 | Abbott et al. |
| 2008/0255591 A1 | 10/2008 | Harada et al. |
| 2008/0281356 A1 | 11/2008 | Chau et al. |
| 2009/0143821 A1 | 6/2009 | Stupak |
| 2009/0248028 A1 | 10/2009 | Alexander |
| 2009/0281377 A1 | 11/2009 | Newell et al. |
| 2009/0281568 A1 | 11/2009 | Cendan et al. |
| 2010/0001038 A1 | 1/2010 | Levin et al. |
| 2010/0076462 A1 | 3/2010 | Bakos et al. |
| 2010/0324597 A1 | 12/2010 | Shikhman |
| 2010/0324598 A1 | 12/2010 | Anderson |
| 2011/0087241 A1 | 4/2011 | Nguyen |
| 2011/0087242 A1 | 4/2011 | Pribanic et al. |
| 2011/0224485 A1 | 9/2011 | Boulnois et al. |
| 2011/0224714 A1 | 9/2011 | Gertner |
| 2011/0283514 A1 | 11/2011 | Fogarty et al. |
| 2012/0080495 A1 | 4/2012 | Holcomb et al. |
| 2012/0089182 A1 | 4/2012 | Page et al. |
| 2012/0101526 A1 | 4/2012 | Bennett |
| 2012/0102526 A1 | 4/2012 | Lejeune |
| 2013/0053884 A1 | 2/2013 | Roorda |
| 2013/0110164 A1 | 5/2013 | Milazzo et al. |
| 2013/0158600 A1 | 6/2013 | Conklin et al. |
| 2013/0180966 A1* | 7/2013 | Gross ............... A61B 17/06166 219/121.69 |
| 2013/0267998 A1 | 10/2013 | Vijay |
| 2013/0282028 A1 | 10/2013 | Conklin et al. |
| 2014/0031864 A1 | 1/2014 | Jafari et al. |

FOREIGN PATENT DOCUMENTS

| | | |
|---|---|---|
| CN | 2558335 Y | 7/2003 |
| DE | 69512446 T2 | 5/2000 |
| DE | 69612447 T2 | 7/2001 |
| EP | 0669101 A1 | 8/1995 |
| EP | 0669103 A1 | 8/1995 |
| EP | 1484023 A1 | 12/2004 |
| WO | 01049207 A2 | 7/2001 |
| WO | 0166001 A2 | 9/2001 |
| WO | 2007002071 A1 | 1/2007 |

OTHER PUBLICATIONS

EP Supplementary Search Report for EP12858766, completed Sep. 7, 2015.
CN Office Action for App. No. 2012800690769, dated Mar. 23, 2015 (translation).
European Supplementary Search Report dated Feb. 9, 2016 for EP13817447.
Int'l. Search Report for PCT/US15/065033, dated Feb. 18, 2016.
Int'l. Search Report for PCT/US2016/022495, dated Jun. 1, 2016.
Ohinese Office Action for Application No. 2013800370375, dated Mar. 28, 2016.
European Search Report issued for Application No. 12858766.4, dated Sep. 16, 2015.
Int'l. Search Report for PCT/US2012/070354, dated Apr. 4, 2013.
Int'l. Search Report from PCT Application No. PCT/US2013/049958, dated Oct. 8, 2013.
Int'l. Search Report for PCT/US2014/046423, dated Oct. 20, 2014.
Int'l. Search Report for PCT/US14/66122 dated Feb. 11, 2015.
LSI Solutions T-Knot Device 2, LSI Solutions, Inc., 2009-2011, http://www.lsisolutions.com/tkoutsideofcannula.
LSI Solutions T-Knot Device, LSI Solutions, Inc., 2009-2011, http://www.lsisolutions.com/tkatscrubtable.
TK Quick Load, LSI Solutions, http://www.lsisolutions.com/tkquickload.
Int'l. Search Report for PCT/US2015/032271, dated Sep. 1, 2015.
International Search Report for International Application No. 16765598.4—1122/3270797 PCT/US2016022495, completed Nov. 27, 2018.

* cited by examiner

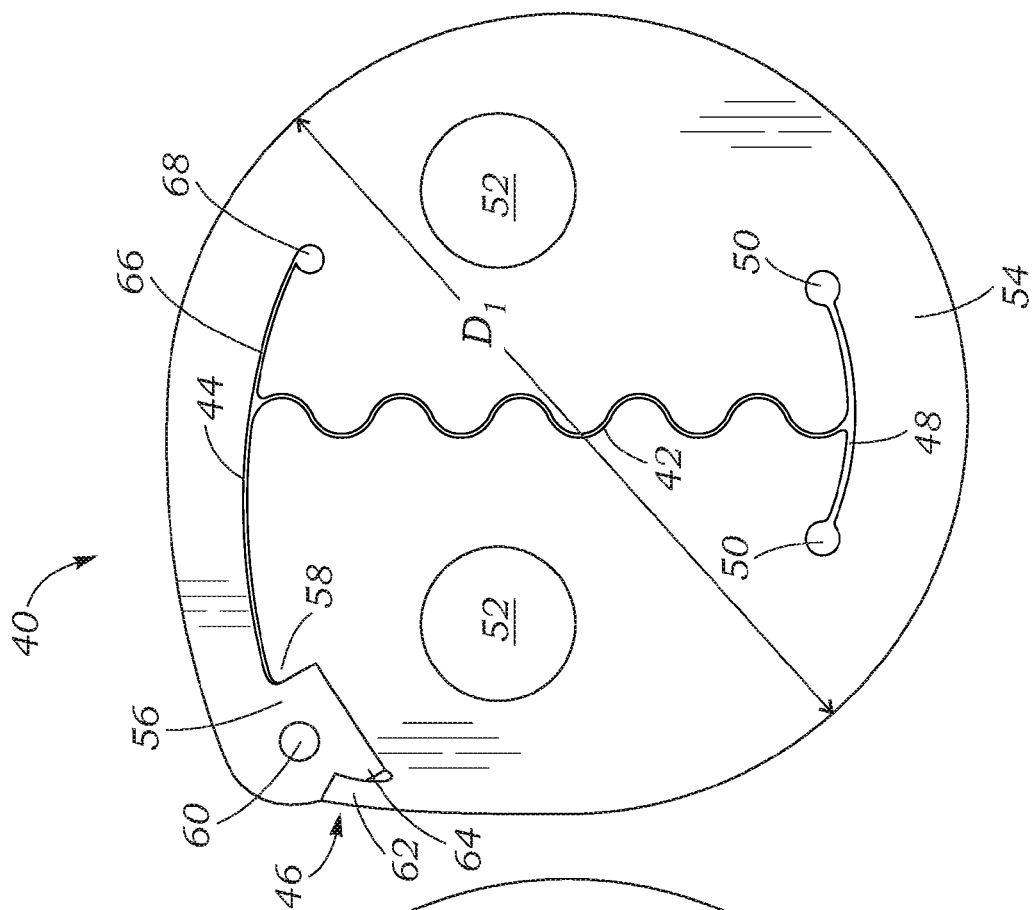
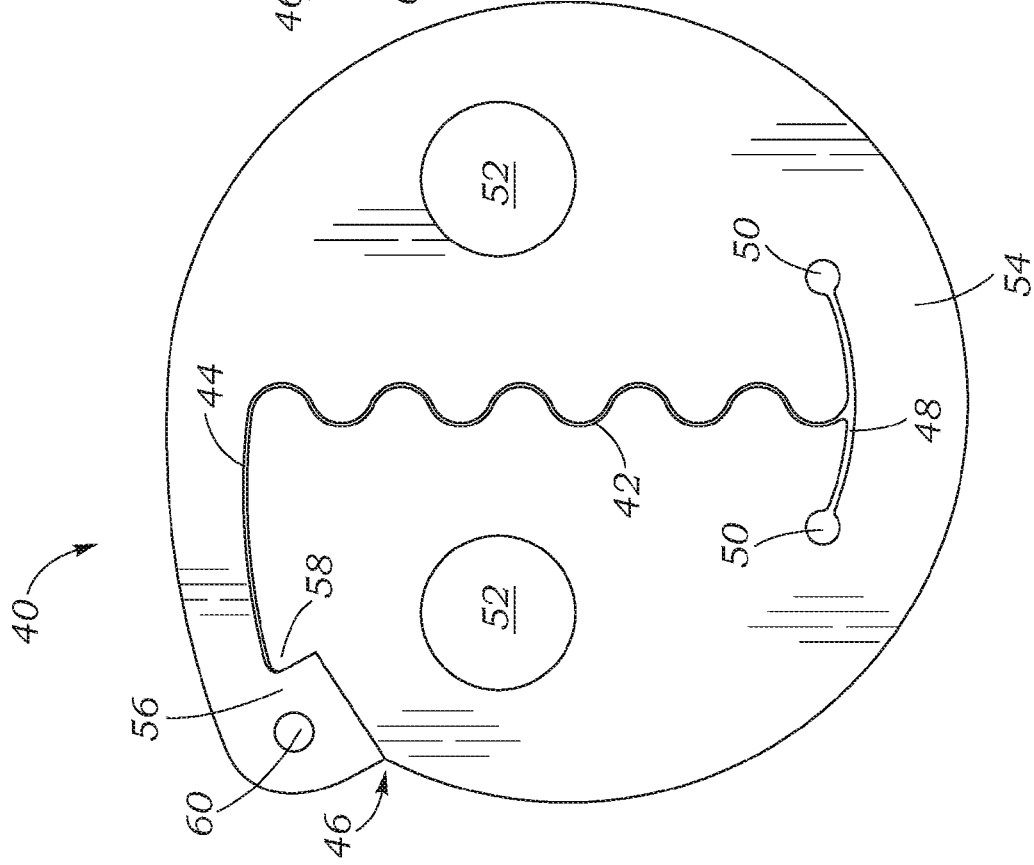

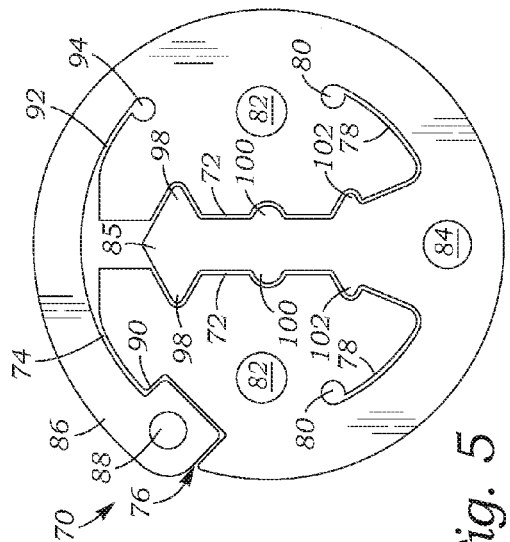
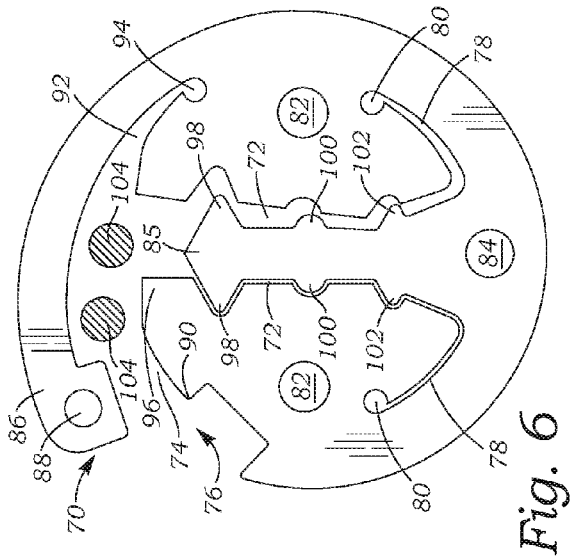
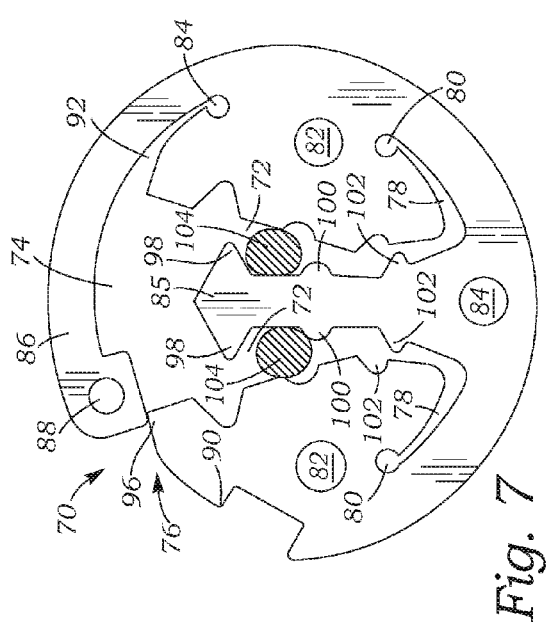
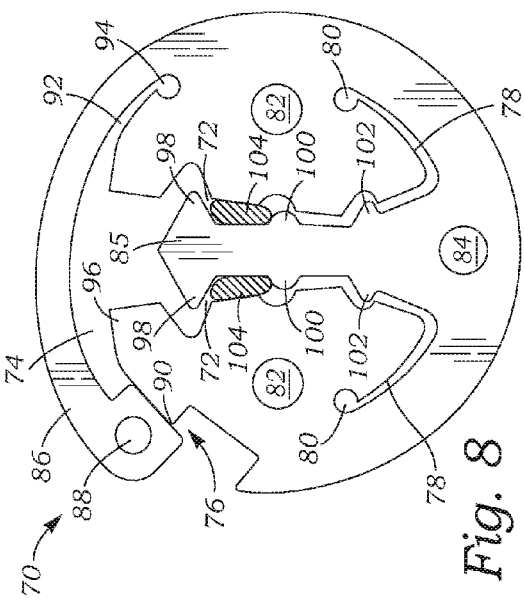

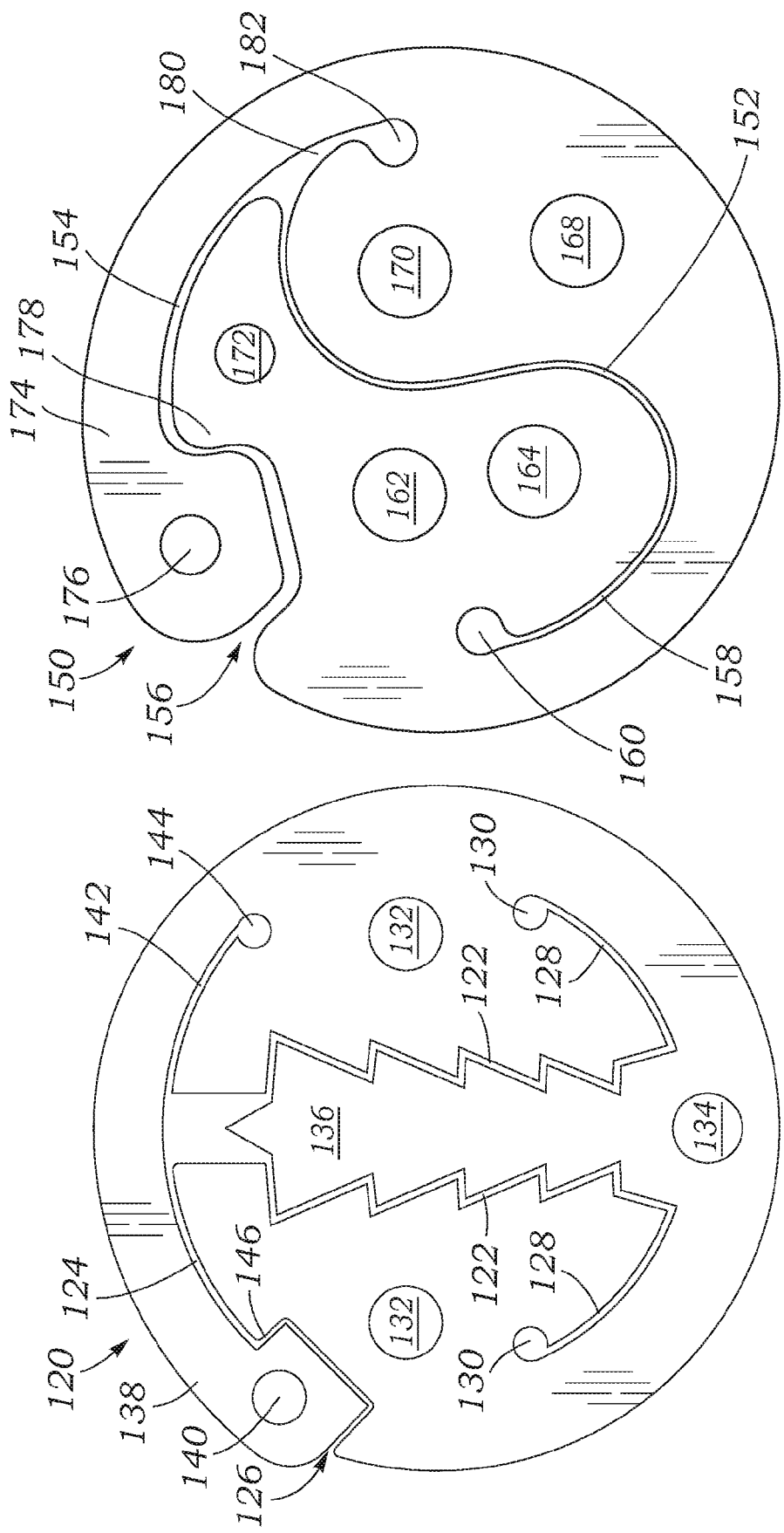

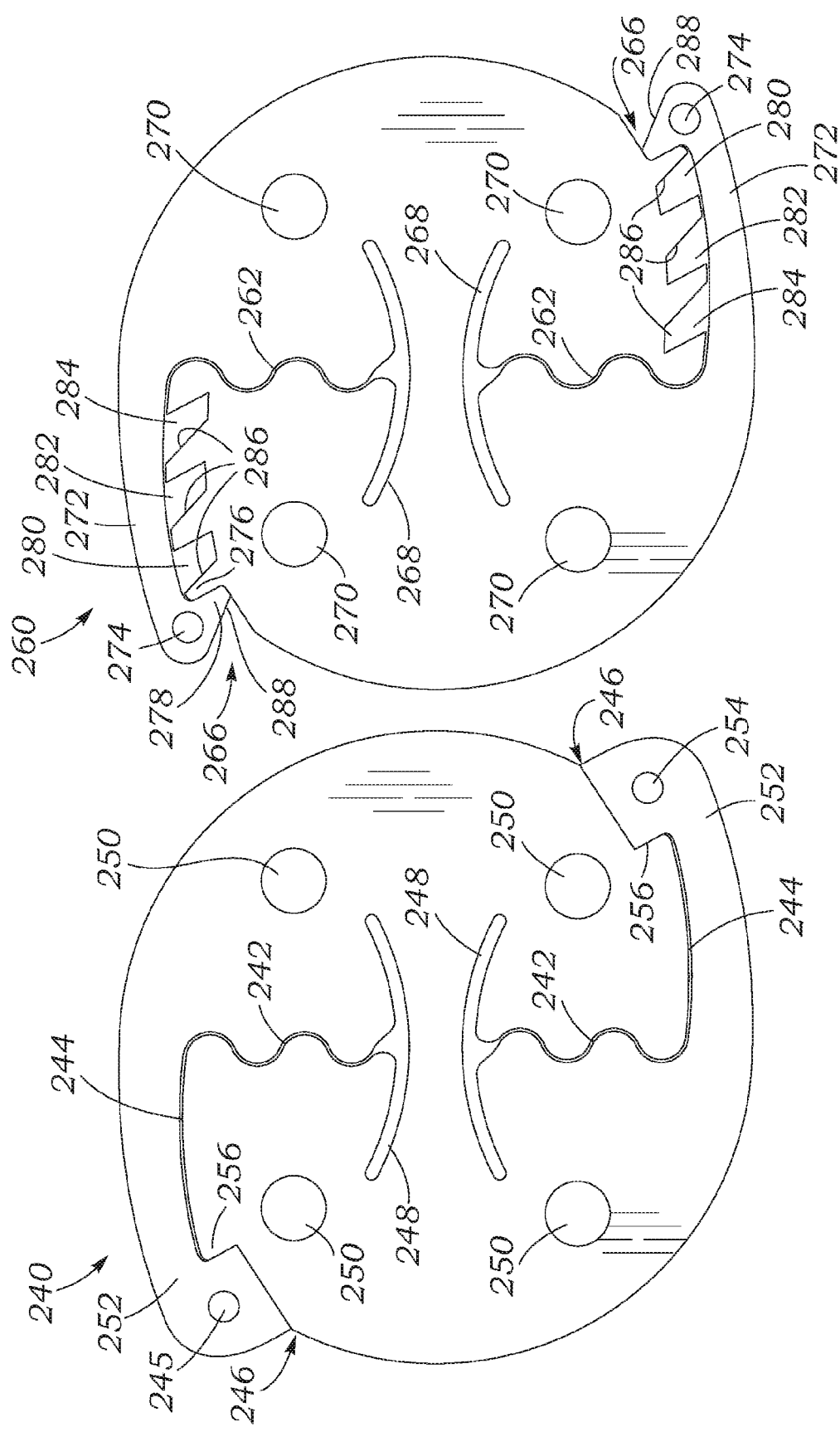

SUTURE SECUREMENT DEVICES

CROSS REFERENCE TO RELATED APPLICATION

This application claims the benefit of U.S. Provisional Patent Application No. 62/133,810, filed Mar. 16, 2015, which is incorporated by reference herein in its entirety.

FIELD

This disclosure relates to devices for securing sutures.

BACKGROUND

Prosthetic devices are often implanted using sutures. For example, prosthetic heart valves and annuloplasty rings can be secured to a native valve annulus using sutures. Conventionally, the loose ends of the sutures are tied in knots to secure them together and/or to secure the prosthetic device to the adjacent tissue. However, the process of tying knots in sutures can be time consuming and difficult, the amount of slack left in the sutures can be difficult to control, the knots can be difficult or impossible to untie, and/or the knots can accidentally come loose. Thus, there is a need in the art for ways to secure sutures without tying knots.

SUMMARY

Disclosed herein are exemplary embodiments of suture securement devices that replace the need to tie knots in sutures.

Some disclosed suture securement devices comprise a flat, thin, generally planar body that has one or more suture engagement slots extending into the body from a perimeter inlet for receiving sutures laterally into the device. The slots can be resiliently widened to receive a suture and then released to clamp onto the suture. Some embodiments include two or more such suture engagement slots that independently receive and secure different sutures. Some embodiments include one or more suture locks that have a closed position that retains the slots against widening and blocks the inlet to the slot. In some embodiments, two or more slots are positioned next to each other on the same side of the device, while in other embodiments slots are positioned on opposite sides of the device.

Some embodiments can comprise an adjustable locking tab that allows the slots to be locked in different closed positions with different maximum slot widths, such that the device can be used with different diameter sutures. In some embodiments, the locking tab forms a ratcheting device that allows the slots to be tightened with simple compression on the device, but resists widening of the slots without first unlocking the locking tab.

Some suture securement devices disclosed herein include a stent-like annular body having a plurality of suture engagement members projecting from one side of the annular body and curving toward each other, such that a suture engagement opening is formed between free ends of the plurality of suture engagement members. The annular body can be resiliently compressible and/or expandable in a radial dimension to cause the free ends of the suture engagement members to move radially apart from each other so that a suture can be inserted into the space between the free ends. Then, when the annular body is released and allowed to resiliently return toward its natural state, the free ends close back together and pinch the suture to secure it.

Still other suture securement devices disclosed herein include a fully enclosed suture engagement opening that does not have a lateral inlet. The enclosed opening can be resiliently widened by pinching, stretching, and/or bending the device so that a suture can be inserted into the opening. Then, releasing the device allows it to resiliently close onto and secure the suture.

Disclosed suture securement devices can eliminate the need to tie knots, can provide a more secure engagement of the sutures, can be adjustable to fit different sizes and numbers of sutures, can be released and resecured to sutures adjust the tension in the sutures, and/or can independently secure two or more sutures using different engagement slots.

The foregoing and other objects, features, and advantages of the disclosed technology will become more apparent from the following detailed description, which proceeds with reference to the accompanying figures.

BRIEF DESCRIPTION OF THE DRAWINGS

FIGS. 3 and 4 are plan views of exemplary suture clips having one suture engagement slot and one locking tab.

FIGS. 5-8 are plan views of an exemplary suture clip having two suture engagement slots and one locking tab, showing various stages of inserting sutures into the slots.

FIG. 9 is a plan view of an exemplary suture clip having two jagged suture engagement slots and a locking tab.

FIG. 10 is a plan view of an exemplary suture clip having a curved suture engagement slot and a locking tab.

FIG. 13 is a plan view of an exemplary suture clip having two opposing suture engagement slots and two locking tabs.

FIG. 14 is a plan view of another exemplary suture clip having two opposing suture engagement slots and two locking tabs, wherein the locking tabs form ratcheting mechanisms.

DETAILED DESCRIPTION

Figure 2:
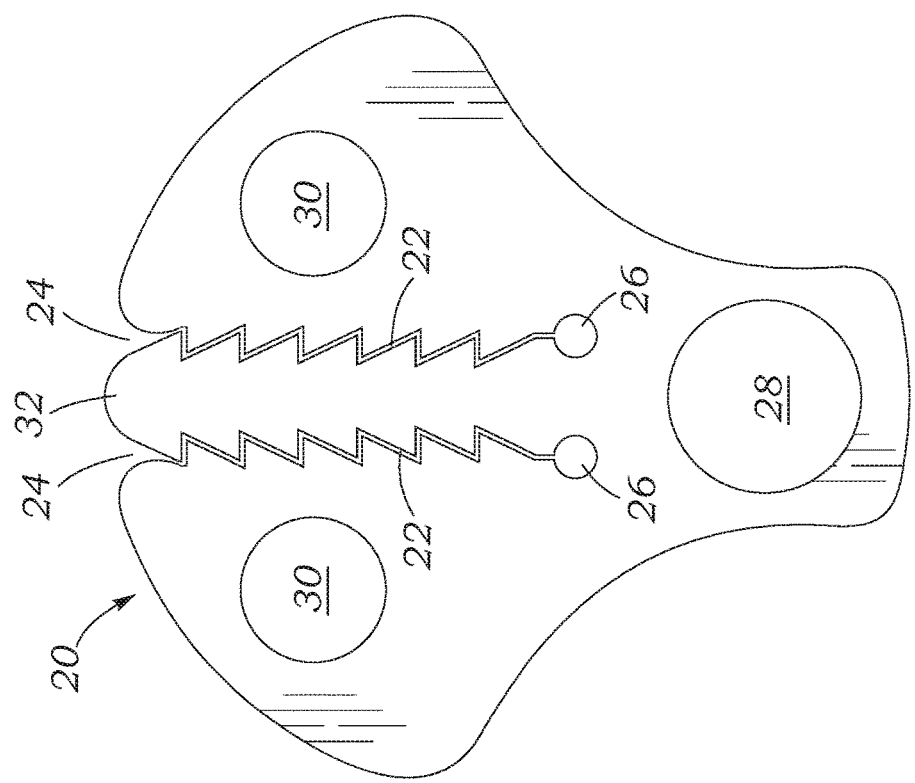
FIG. 2 is a plan view of an exemplary suture clip having two suture engagement slots.

Rather than tying knots to secure sutures, suture securement devices (also referred to herein as "suture clips") can be placed on sutures to secure them. Several exemplary embodiments of suture clips are disclosed herein and shown in the attached figures. These embodiments should not be construed as limiting in any way. Instead, the present disclosure is directed toward all novel and nonobvious features and aspects of the various disclosed embodiments, alone and in various combinations and sub-combinations with one another.

The disclosed suture clips can secure a single suture or two or more sutures at the same time. Furthermore, some of the disclosed suture clips include two or more slots or other suture engagement regions, each of which is configured to receive and engage at least one suture independently. For ease of description, however, this disclosure generally describes the various embodiments in exemplary uses with only one suture engaged in each slot or other independent engagement region, though it should be understood that the disclosed embodiments may be used with any number of sutures in each engagement region in the same or similar manner, unless otherwise described.

Suture clips disclosed herein can be used to secure sutures for various purposes. For example, the suture clips can be used to secure a prosthetic device to native tissue in the body. Applicable prosthetic devices can include, for example, annuloplasty rings, prosthetic heart valves, stents, grafts, and various other prosthetic implants, which conventionally are secured to native tissue using sutures. Any number of suture clips can be used to secure a prosthetic device to native tissue, for example. For example, an annuloplasty ring may be secured to a native mitral valve annulus using twelve sutures clips arrayed around the ring. In some examples, each suture clip can secure together two sutures extending from opposite directions, in place of a standard knot. In other examples, a separate clip can be secured to each suture at the location where the particular suture passes through a prosthetic device or exits from native tissue. In some embodiments, suture clips also allow sutures to be further tightened after an initial deployment to reduce any excess slack in the sutures.

The disclosed suture clips can be positioned on a suture by sliding the suture laterally through a slot in the clip and/or, in some cases, by optionally threading a free end of a suture axially through an opening in the clip.

Some disclosed suture clips are configured to be elastically deformed to receive sutures into an engagement region within the clip and some embodiments are configured to remain slightly elastically deformed after they are deployed onto a suture. Such deployed suture clips are thereby biased against the suture to grip the suture and prevent the suture from sliding through the clip. As used herein, the terms "elastic," "elastically," and "elasticity" are used in a broad sense to indicate any resilient deformation that tends to naturally return to its pre-deformed state, and these terms include the related concepts of superelasticity and pseudoelasticity.

Some disclosed suture clips can include a locking mechanism to ensure that the sutures remain sufficiently pinched by the suture clips and cannot come loose. Further, some embodiments include a locking mechanism that can be locked in any one of a plurality of different locked positions, each corresponding to a different size of aperture where the sutures are secured. This can enable a single, adjustable suture clip to be used with several different diameters of sutures while maintaining an even engagement force.

By using the disclosed suture clips rather than tying knots in the sutures, the sutures can be secured in less time, with less difficulty (especially in hard-to-reach locations), and/or in a more secure manner. In addition, some suture clips can allow the amount of slack left in the sutures to be more precisely controlled, the suture clips can be less likely to come loose than knots, and many embodiments can be easily removed or adjusted after they are initially deployed. Furthermore, the suture securement devices can be small, durable, biocompatible, and inexpensive.

Disclosed suture clips are shown generally in a plan view and can vary in thickness (dimension perpendicular to the page in FIGS. 1-14 and 16), though the thickness is generally smaller than the illustrated dimensions perpendicular to the thickness. Any of the clip embodiments described herein can have a thickness of, for example, from about 0.001 inches to about 0.100 inches, such as about 0.010 inches. Increased thickness generally results in a more rigid clip that provides greater clamping force and greater resistance to engaged sutures sliding through the device after deployment. Disclosed suture clips can also vary in the dimensions perpendicular to the thickness dimension. In some embodiments, the device can have an average outer diameter of about 2 mm to about 5 mm, or they can be larger or smaller.

The disclosed suture clips can comprise any resiliently deformable, corrosion-resistant, biocompatible material, such as stainless steel, cobalt-chrome (Co—Cr), Elgiloy, MP35N, and/or Nitinol. Some embodiments can comprise more than one material, such as a more rigid material for the one portion and a more flexible material for another portion. Desirably, the suture clips are comprised of material with a recoverable strain that is sufficient to retain sutures, such as a recoverable strain that ranges from about 5% to about 15%.

More information regarding exemplary suture securement devices and exemplary methods of use can be found in U.S. Patent Application Publication No. 2014/0031864, published on Jan. 30, 2014, which is incorporated by reference herein in its entirety.

Figure 1:
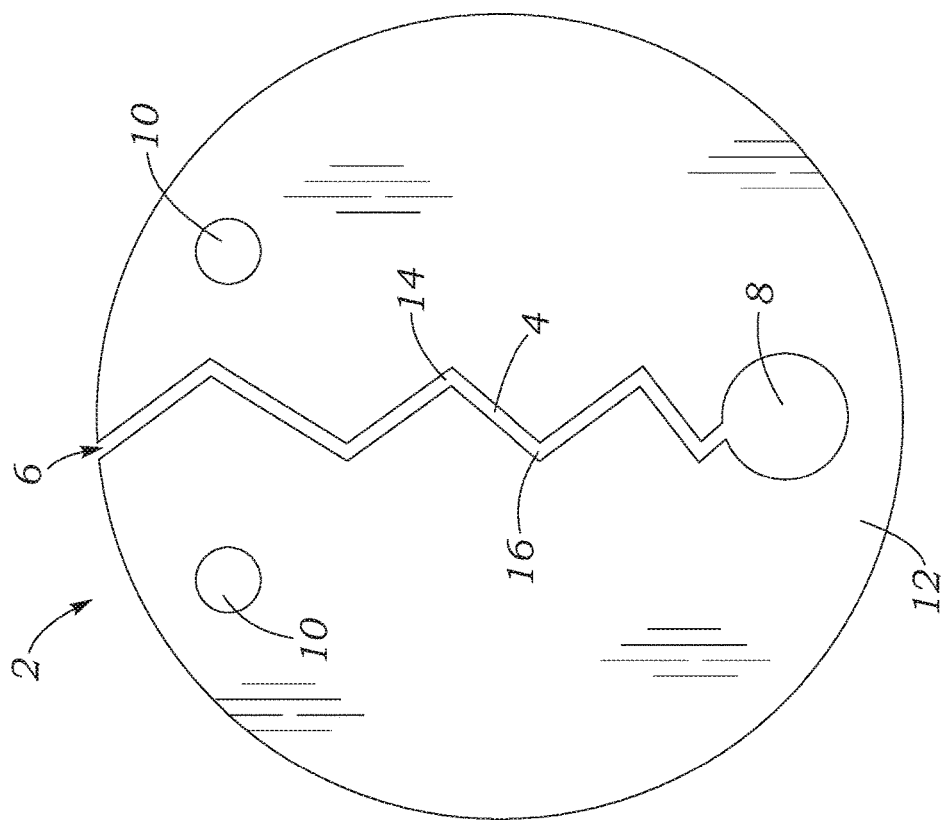
FIG. 1 is a plan view of an exemplary suture clip having one suture engagement slot.

FIG. 1 shows an exemplary suture clip 2 that includes a jagged slot 4 extending from an inlet 6 at a radial edge of the clip. The clip 2 also includes a relief opening 8 at the end of the slot 4 that helps distribute strain broadly across a deformation region 12 of the clip when the slot 4 is forced open to receive a suture. The clip 2 can also include two openings 10 on opposite sides of the slot 4 near the inlet 6 that can be used to engage the clip with a tool. Such a tool can apply a separation force to open up the slot 4, and can also be used to hold the clip and position the clip at a desired location in the body prior to deployment. The slot 4 (and other slots disclosed herein) can have a natural width that is less than the width of an associated suture, and can be resiliently spread apart to a width that is greater than the width of the suture so that the suture can laterally enter the slot through inlet 6. The suture can be located anywhere along the slot, such as in a generally central part of the clip (e.g., between corners 14 and 16 of the slot), prior to releasing the separation force and allowing the two sides of the clip to resiliently close back toward the natural position of the clip and thereby pinch the suture within the slot. The corners (e.g., corners 14, 16) along the jagged slot 4 can help prevent the suture from sliding laterally out of the slot through the inlet 6 or into the relief opening 8. In the clip 2, the retention force applied to the sutures by the clip is primarily generated by the elasticity of the deformation region 12 that bridges the two sides of the clip together.

FIG. 2 shows an exemplary suture clip 20 that includes two jagged slots 22 that extend generally parallel from inlets 24 located at one side of the clip. Each slot 22 can receive and grip a suture independently. Each slot 22 includes a relief opening 26 at the inner end of the slot to help distribute strain over a broader area around the ends of the slots. The clip 20 can include openings, such as openings 28 and 30, that can be used to engage the clip with a deployment tool. The openings 30 are located on opposite sides of the slots 22 and can be used to pull the two sides of the clip apart from a central portion 32 to open the slots 22. The slots 22 can have a jagged pattern that helps prevent engaged sutures from exiting out through the inlets 24. The jagged pattern, for example, can include portions that are perpendicular, or close to perpendicular, to the overall direction of the slot. Due to these slot portions, a suture is restricted from sliding along the slot toward the inlet 24 due to a force applied to the suture in the direction from the relief opening 26 toward the inlet 24. The clip 20 is shown having an irregularly shaped outer periphery, though in other embodiments the clip 20 can have a circular or other shaped outer periphery.

FIG. 3 shows an exemplary suture clip 40 that includes a single slot 42 along with a locking tab 56. The slot 42 has a wavy or sinusoidal pattern that extends from a relief slot 48 at one end and an outer slot 44. The outer slot 44 communicates with an inlet 46 to allow insertion of a suture into the slot 42. The relief slot 48 can extend generally perpendicular to the slot 42 and can include relief openings 50 at either end to help distribute strain over a broader area when the slot 42 is opened. Openings 52 on either side of the slot 42 can be engaged with a delivery tool and used to apply a separation force to open the slot 42. When the slot 42 is opened, the majority of the deformation can occur in a lower connector portion 54 below the relief slot 48. The locking tab 56 can engage with a notch 58 in the body of the clip to lock the slot 42 closed. To open the slot 42 and insert a suture, the locking tab 56 is first deflected radially outwardly, such as by using an opening 60 in the locking tab. During this process, the inlet 46 and the outer slot 44 spread open while the slot 42 remains substantially closed. When the locking tab 56 is lifted far enough to clear the notch 58, the right-hand side of the clip 40 can then be separated from the left-hand side of the clip to open the slot 42. A suture can then be inserted through the inlet 46 and into the slot 42. Releasing the separation force on the clip can allow the slot 42 to resiliently close and pinch the suture. Optionally with the help of additional clamping force applied by a delivery tool, the clip 40 can close far enough to allow the locking tab 56 to move into engagement with the notch 58 to lock the suture engaged in the slot 42 and maintain a desired pinching force on the suture.

FIG. 4 shows a variation of the clip 40 that includes a locking tab retainer 62 as well as a locking tab relief slot 66. The retainer 62 can extend from the main body of the clip 40 and engage with a notch 64 in the locking tab 56 to help retain the locking tab in the locked position and resist accidental unlocking of the locking tab Like the locking tab 56, the retainer 62 can be resiliently flexible such that a certain amount of minimum force needs to be applied to the locking tab 56 to cause the retainer 62 to disengage from the notch 64 and allow the locking tab to be deflected outwardly to clear the notch 58. The locking tab relief slot 66 makes the locking tab 56 longer and allows the locking tab a greater degree of independent flexibility. The end of the relief slot 66 can include a relief opening 68 to reduce stress concentrations at the end of the relief slot when the locking tab 56 is deflected outwardly to unlock the clip.

FIGS. 5-8 show another exemplary suture clip 70 in four positions that illustrate the insertion of two 104 sutures into the clip. The clip 70 includes two suture engagement slots 72, an outer slot 74 coupled to both slots 72, an inlet 76 coupled to the outer slot 74, relief slots 78 and relief opening 80 as the lower ends of the engagement slots 72 opposite from the outer slot 74, and a locking tab 86. The clip 70 can also include openings, such as openings 82 and 84, that can be used to engage the suture clip with a delivery tool. The openings 82 are located on opposite sides of the engagement slots 72 and can be used to separate the left and right sides of the clip apart from a central portion 85 that extends between the slots 72. The locking tab 86 can include an opening 88 that can be used to engage the locking tab with a tool. The locking tab 86 also includes a relief slot 92 and a relief opening 94, similar to the clip 40 in FIG. 4.

FIG. 5 shows the clip 70 is a closed and locked position without sutures engaged by the clip. FIG. 6 shows an unlocked position where the locking tab 86 has been deflected outwardly sufficiently to clear the notch 90 in the body of the clip and to allow the sutures 104 to enter through the inlet 76 and into the opened outer slot 74. As shown in FIG. 6, deflecting the locking tab 86 can also partially open at least the right-hand engagement slot 72.

As shown in FIG. 7, further separation of left and right portions of the clip 70 causes the engagement slots 72 to open sufficiently to allow the sutures 104 to enter into and be positioned at a desired location along the engagement slots. The engagement slots 72 can include one or more non-straight, or jagged, portions to help grip and retain engaged sutures. For example, the illustrated engagement slots 72 include non-straight portions 98, 100, and 102. The sutures 104 can be engaged anywhere along the slots 72, such as in the regions between the non-straight portions 98 and 100 (as illustrated), in the regions between the non-straight portions 100 and 102, and/or in the non-straight portions themselves.

As shown in FIG. 7, it can be desirable for the end of the locking tab 86 to remain in contact with the outer surface 96 of the left-hand part of the clip so that the locking tab, which can be resiliently biased inwardly, does not move inwardly toward the slots 72 and the central portion 85.

As shown in FIG. 8, when the sutures 104 are in a desire location along the slots 72, the clip can be allowed to close, with optional user assistance, thereby pinching and engaging the sutures. Further closing clip 70 allows the locking tab 86 to engage with the notch 90 to lock the clip closed.

FIG. 9 shows another exemplary suture clip 120 that is similar to the clip 70 shown in FIGS. 5-8. The clip 120 includes two jagged suture engagement slots 122 with relief slots 128 and relief openings 130, an outer slot 124, an inlet 126, and a locking tab 138 with a relief slot 142 and a relief opening 144. The clip 120 can include openings, such as openings 132 and 134, for engaging the clip with a deployment device. The openings 132 can be used to pull the left and right sides of the clip apart from a central portion 136 to open the jagged slots 122. The locking tab 138 can include an opening 140 that can be used to pull the locking tab outward to clear the notch 146 in order to unlock the clip.

FIG. 10 shows an exemplary suture clip 150 having a single, curved suture engagement slot 152 and generally curved surfaces throughout the clip. The curved engagement slot 152 can have an "S" shape with a relief portion 158 and a relief opening 160 at one end and the opposite end joining with an outer slot 154, an inlet 156, and a relief slot 180 and relief opening 182 for the locking tab 174. The locking tab 174 includes an opening 176 that can be used to pull the locking tab outwardly to clear a notch 178 in the main body to unlock the clip. The clip 150 can include a plurality of openings, such as two or more of the illustrated openings 162, 164, 168, 170, 172, which can be used to engage the clip with a delivery device and can be used to separate the curved engagement slot 152 to insert a suture. Various openings can in different positions can be included, as shown, to allow a delivery device to apply separation force and torque along different axes to open and close the curved slot 152 and/or the locking tab 174 in different ways.

Figure 11:
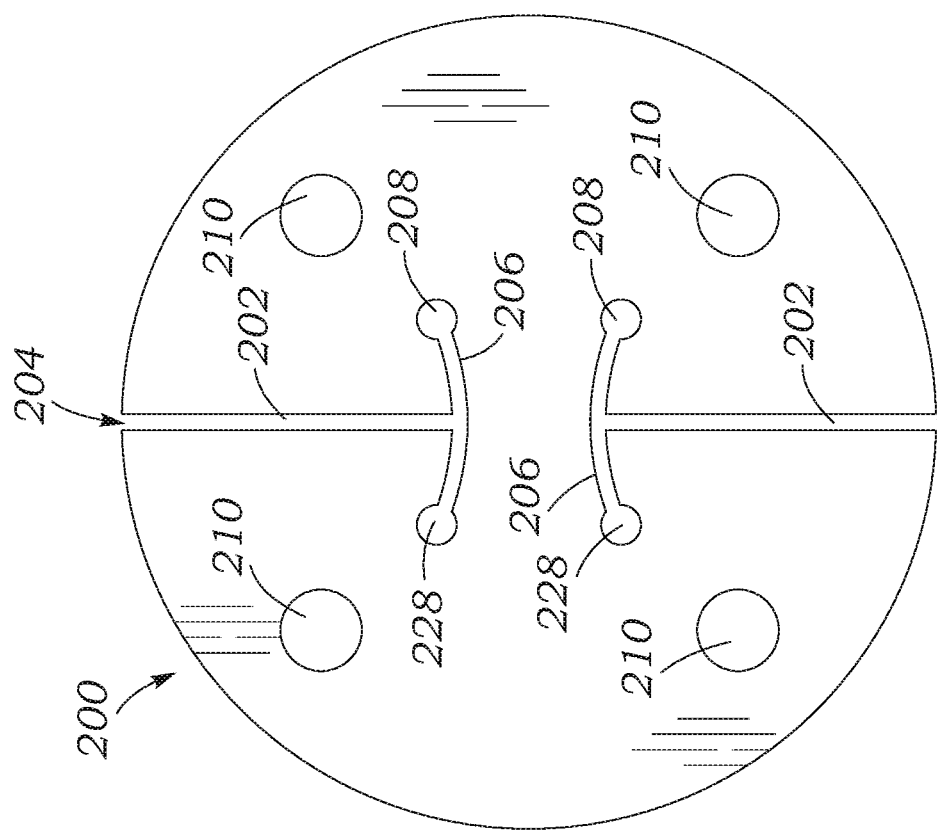
FIG. 11 is a plan view of an exemplary suture clip having two opposing suture engagement slots.

FIG. 11 shows an exemplary suture clip 200 that include suture engagement slots 202 extending into the clip from inlets 204 on opposite sides of the clip. Each suture engagement slot 202 includes a relief slot 206 with relief openings 208 at the inner ends of the slots. Left and right portions of the clip 200 are bridged by a connector between the relief slots 206. The clip 200 can include openings 210 on opposite sides of the suture engagement slots 202 to hold the clip with a delivery device and/or to open the slots 202 to receive sutures. With the opposing slots 202, sutures can be inserted into the clip from opposing directions, instead from a common inlet or side of the clip as described in other embodiments herein.

Figure 12:
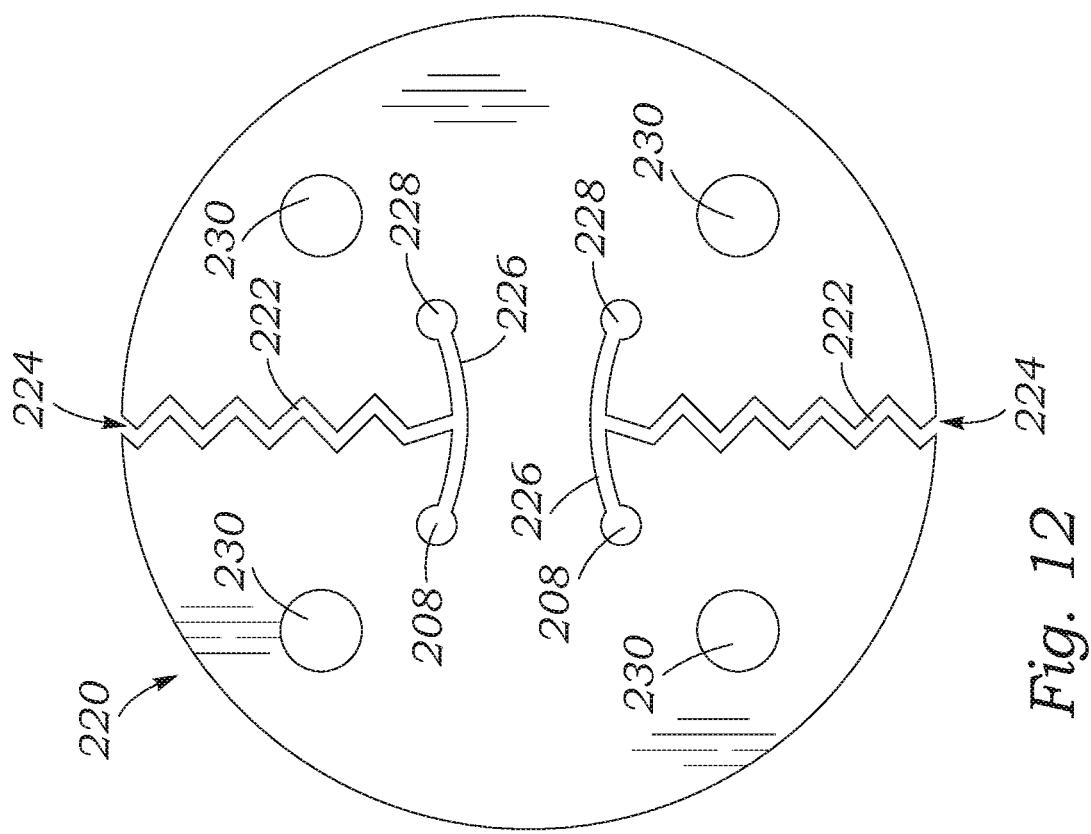
FIG. 12 is a plan view of an exemplary suture clip having two opposing jagged suture engagement slots.

FIG. 12 shows another exemplary suture clip 220 that also includes two opposing suture engagement slots 222. However, the slots 222 are jagged, as opposed to the straight slots 202 in the clip 200. Each suture engagement slot 222 can include a relief slot 226 with relief openings 228. The clip 220 can include openings 230 on opposite sides of the suture engagement slots 222 to hold the clip with a delivery device and/or to open the jagged slots 222 to receive sutures.

FIG. 13 shows an exemplary suture clip 240 that includes two opposing suture engagement slots 242, each having its own locking tab 252. The suture engagement slots 242 have a wavy or sinusoidal shape and extend between relief slots 248 at their inner ends and outer slots 244 that connect to inlets 246. Openings 250 can be located on either side of the slots 242 and can be used to engage the clip 240 with a delivery tool and to open the slots 242. The locking tabs 252 can include openings 254 to pull the locking tab outwardly to clear the notches 256 in order to unlock the locking tabs and open up the inlets 246 and outer slots 244.

FIG. 14 shows another exemplary suture clip 260 that includes two opposing suture engagement slots 262, each having its own locking tab 272 with a ratcheting feature. The suture engagement slots 262 extend between relief slots 268 at their inner ends and outer ratcheting regions that connect to inlets 266. Openings 270 can be located on either side of the slots 262 and can be used to engage the clip 260 with a delivery tool and to open the slots 262. The locking tabs 272 can include openings 274 to pull the locking tab outwardly to unlock the locking tabs and open up the inlets 246 and the ratcheting regions. Each locking tab 272 includes a prong 278 that can positioned in several different locking positions corresponding to different widths of the corresponding suture engagement slot 262. In the tightest locked position, as shown, the prong 278 is engaged with the projection 276 that extends from the body of the clip. The locking tab 272 can also be positioned in looser locked positions where the prong is in one of the notches 280, 282, 284 in the main body. Each of the notches 280, 282, 284 is slanted toward the inlet 266 and has a sloped side surface 286 on the inlet side of the notch. The sloped side surfaces 286 allow the prong 278 to slide up out of the notches along the sloped surface and then snap back down into the next tightest locked position when a compressive force is applied to the opposing sides of the suture engagement slot 262, such as by using a tool to apply compressive forces at the openings 270. This creates a ratcheting mechanism where the locking tab 272 is permitted to move to tighter locked positions when applying compressive forces, but the locking tab 272 is prevented from moving to looser locked positions without first manually lifting the prong 278 outward out of is current lock position. The various different locked positions for the locking tabs allows the clip 260 be usable with suture having a range of different diameters. Larger diameter sutures can be sufficiently secured with the prong 278 positioned in the notch 284, for example.

Figure 15:
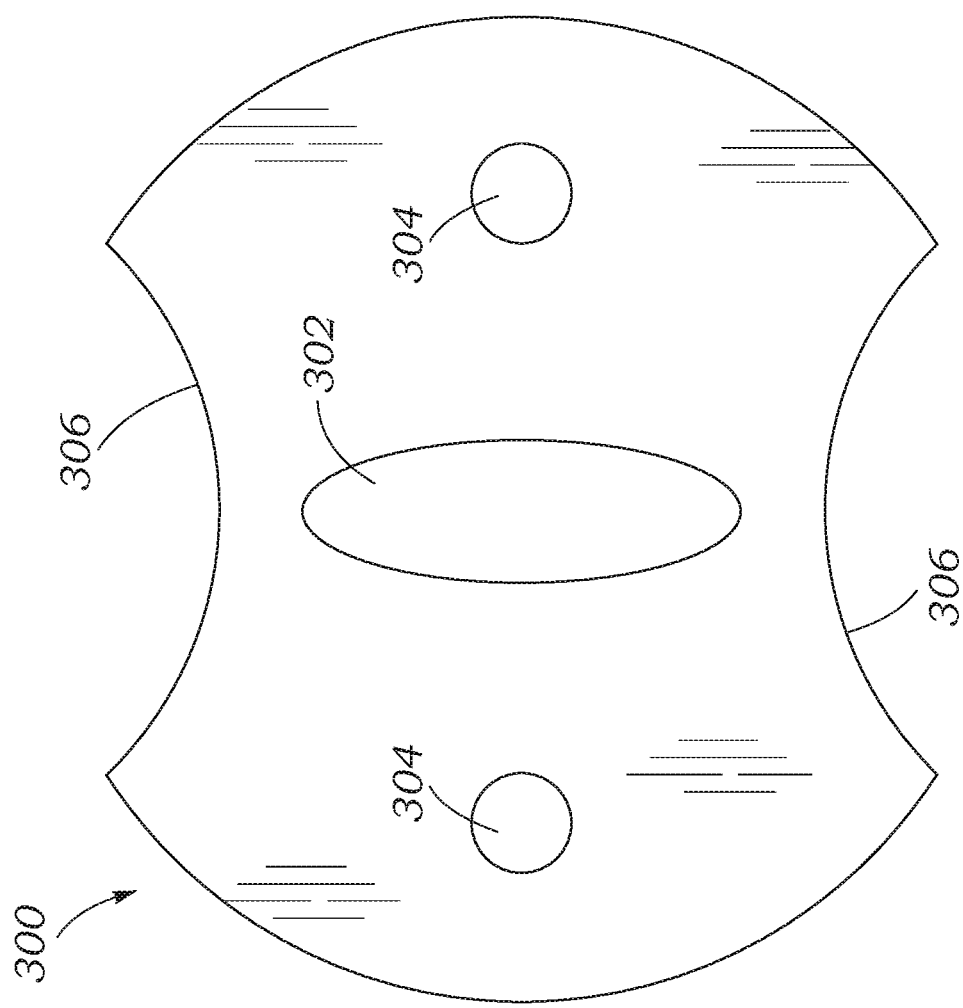
FIG. 15 is a plan view of an exemplary suture clip having an enclosed suture engagement opening.

FIG. 15 shows another exemplary suture clip 300 that includes an elliptical central opening 302 for engaging a suture. With the clip 300, an end of a suture is inserted axially through the opening 302, rather than being inserted laterally into a slot, as in other embodiments disclosed herein. In its natural state, the width (minor axis) of the elliptical opening 302 can be narrower that the diameter of an associated suture in order to pinch and secure a suture in the opening. To widen the opening 302 for suture insertion or adjustment, compressive forces can be applied to the clip at recesses 306 in the direction of the length (major axis) of the opening 302, and/or tensile forces can be applied to the clip via openings 304 on opposite sides of the width of the opening 302. In some methods, the clip 300 can be bent or curled in order to change the shape of the opening 302.

Figure 16:
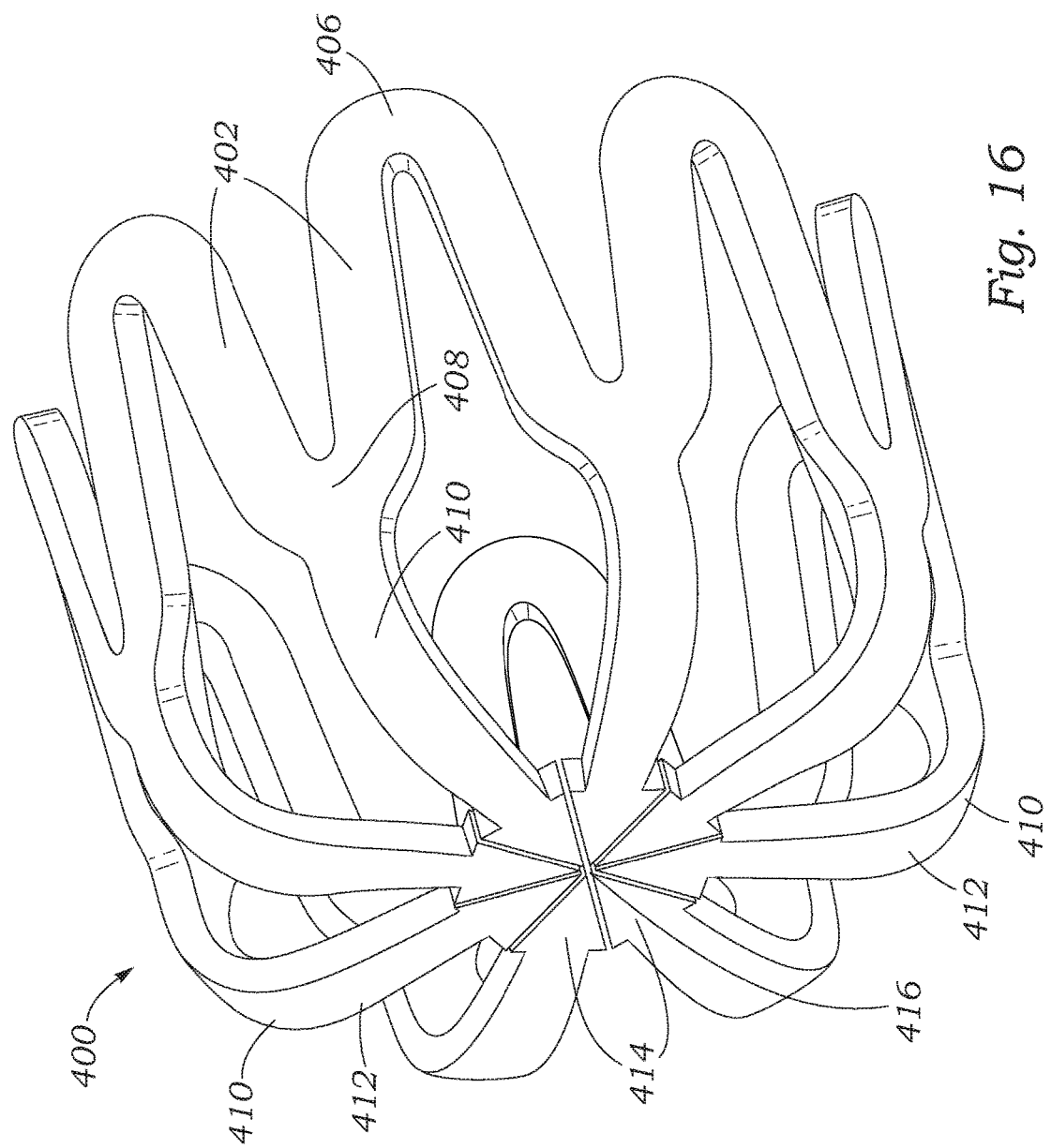
FIG. 16 is a perspective view of an exemplary suture clip having a compressible and expandable stent-like annular body and a plurality of suture engagement arms with free ends that engage a suture between them.

FIG. 16 shows another exemplary suture clip 400 that includes a suture engagement opening 416 formed between a plurality of radially inwardly pointing engagement members 410. The engagement members 410 are curved or bent at their radially outer ends and are joined to a flexible, stent-like ring 402 that can radially expand and contract. The ring 402 has a snaking or zigzag shaped structure that provides radial elasticity. The engagement members 410 attach to one axial end 408 of the ring 402 and the opposite axial end 406 of the ring is open. The engagement members 410 can include tapered heads 414 at their radially inward ends, which can be generally arrow shaped and terminate at points/edges, as illustrated, to grip the suture. The heads 414 can be separated to open the suture engagement opening 416, such as by compressing and/or expanding the ring 402 or by applying a radially outward separation force to the heads from a separation device positioned in the opening 416.

In some embodiments, a tubular device having a tapered/pointed end can be inserted into the opening 416 in order to pry the heads 414 apart. The tubular device can have an inner lumen that contains or receives a suture so that the tubular device allows the suture to be inserted through the opening inside the tubular device while the outer surface of the tubular device holds the heads resiliently spaced apart. The tubular device can then be removed from the opening 416 while the suture remains in the opening 416, thereby allowing the heads to close in on the suture.

In some embodiments, when the heads 414 move radially outwardly and apart from each other, radial slots open up between each adjacent head to optionally allow a suture to slide laterally into the central opening 416. Alternatively, a suture can be axially inserted through the opening 416 while the heads 414 are held apart. Then, when the delivery device is removed, the heads resiliently move radially inwardly toward their natural position and close on the suture in the opening 416.

In any of the disclosed suture clips, the clip can be adjusted after it has been deployed and engaged onto a suture. For example, the tension in the engaged suture can be increased or decreased to a more desirable value by moving the clip axially the suture, and/or the sutures can be moved laterally along the engagement slots to a more desirable position. In the examples shown in FIGS. 1, 2, 11, and 12, the suture engagement slots can simply be widened by applying a separating force (e.g., via the openings 10 in FIG. 1) in order to adjust an already engaged suture. In the examples shown in FIGS. 3-10 and 13-14, the locking tabs may need to be unlocked first, and then a separating force can be applied to the clip to widen the suture engagement slots in order to adjust an already engaged suture. In the example shown in FIG. 14, the locking tabs 272 can be tightened to apply greater clamping force on an engaged suture via the ratcheting mechanism by simply applying a compression force. In the examples shown in FIGS. 15 and 16, compression and/or separation forces can be applied to the clips to cause the suture engagement openings to widen in order to allow an already engaged suture to be adjusted. The adjustability of the disclosed suture clips reduces the need to completely remove and/or replace a deployed suture clip if it is later found that the secured suture needs to be adjusted.

Furthermore, many of the disclosed suture clip embodiments have a flat, planar configuration that allows the clip to be usable equivalently when the clip is flipped over. Such clips can be termed "bi-directional" or "non-directional" because the suture can extend through the clip from either side equivalently, and the clips provide resistance to axial suture movement in both axial directions.

In addition to other features described herein, disclosed suture clips can provide any one or more of the following advantages: there is no need to crimp the clip at deployment or plastically deform the clip, the clips can be retrievable and removable and re-deployable, the clips can be used with any suture type, the free ends of engaged sutures can be cut off close to the clip body, the clips can be safe for use in magnetic resonance imaging and other imaging procedures, the clips can provide at least 4 pounds of retention force or at least 6 pounds of retention force (or other desired retention force levels), the clips can have a thickness of 0.5 mm or less, 1 mm or less, 1.5 mm or less, and/or 2 mm or less, the clips can have a diameter or maximum dimension of 2.5 mm or less, 3 mm or less, 4 mm or less, and/or 5 mm or less, the clips can avoid damage to sutures to which they are applied, the clips can be deployed on sutures without the use of a snare, and/or the clips can be deployed onto a suture laterally after the suture has been placed in a patient's body without having to thread a free end of the suture through a hole in the clip.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Elements, characteristics, dimensions, integers, materials, groups, or other features described in conjunction with a particular aspect, embodiment or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an" and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A," "B," "C," "A and B," "A and C," "B and C" or "A, B and C." As used herein, the term "coupled" generally means physically coupled or linked and does not exclude the presence of intermediate elements between the coupled items absent specific contrary language.

In view of the many possible embodiments to which the principles of the disclosed technology may be applied, it should be recognized that the illustrated embodiments are only preferred examples of the technology and should not be taken as limiting the scope of the disclosure. Rather, the scope of the disclosure is at least as broad as the following claims. We therefore claim all that comes within the scope of these claims.

The invention claimed is:

1. A device for securing sutures, comprising:
a flat, thin, generally planar body comprising a resiliently deformable material;
a first suture engagement slot having a narrow, tortuous shape that extends into the body from a first inlet at a perimeter of the body; and
a second suture engagement slot having a narrow, tortuous shape that extends into the body from the first inlet or from a second inlet at the perimeter of the body;
wherein the first and second suture engagement slots are each configured to receive a suture through an associated inlet and the narrow, tortuous shapes of the suture engagement slots are configured to apply a pinching force to the suture when received in the slot such that the device secures to the suture and resists the suture from moving axially through the device along a longitudinal axis of the suture and resists the suture from moving laterally out of the device through the associated inlet; and
wherein the device further comprises a first hole passing through the body and a second hole passing through the body, the first and second holes being positioned on opposing sides of the first suture engagement slot and spaced apart laterally from the first suture engagement slot, wherein the first and second holes are configured to receive a tool that applies a separation force to the first suture engagement slot.

2. The device of claim 1, wherein the narrow, tortuous shapes of the first and second suture engagement slots comprise at least three alternating apices.

3. The device of claim 1, wherein the first and second suture engagement slots are generally parallel to each other.

4. The device of claim 1, wherein the first and second suture engagement slots are positioned side-by-side and the first and second inlets are adjacent to each other on one side of the perimeter.

5. The device of claim 1, wherein the first and second suture engagement slots are positioned on opposite sides of the device and the first and second inlets are positioned opposite sides of the perimeter.

6. The device of claim 1, wherein inner ends of the first and second suture engagement slots join relief openings fully contained within the body that reduce stress concentrations in the body when the first and second suture engagement slots are widened, and wherein the relief openings have a width greater than a width of the suture engagement slots.

7. The device of claim 1, wherein the body includes at least a first locking tab that has a closed position wherein at least the first suture engagement slot is retained against widening and at least the first inlet is blocked.

8. The device of claim 7, wherein the first locking tab has two or more closed positions wherein an associated suture engagement slot is retained against widening, and the associated suture engagement slot has a different width when the first locking tab is in each of the two or more closed positions.

9. The device of claim 1, wherein the body includes a first locking tab that has a closed position wherein the first suture engagement slot is retained against widening, and wherein the body includes a second locking tab that has a closed position wherein the second suture engagement slot is retained against widening.

10. The device of claim 1, wherein the tortuous shapes of the first and second suture engagement slots include portions that extend substantially perpendicularly to an overall direction of the slot.

11. The device of claim 1, wherein the first and second holes are also positioned on opposing sides of the second suture engagement slot and spaced apart laterally from the second suture engagement slot, wherein the first and second holes are configured to receive a separation device that widens the first and second suture engagement slots.

12. The device of claim 1, further comprising a third hole passing through the body and a fourth hole passing through the body, the third and fourth holes being positioned on opposing sides of the second suture engagement slot and spaced apart laterally from the second suture engagement slot, wherein the third and fourth holes are configured to receive a separation device that widens the second suture engagement slot.

13. The device of claim 1, wherein the first and second holes are discrete from the first and second suture engagement slots, such that a suture positioned in the either of the first and second suture engagement slot cannot move laterally into either of the first and second holes.

14. A device for securing sutures, comprising:
a flat, thin, generally planar body comprising a resiliently deformable material;
a suture engagement slot that extends into the body from an inlet at a perimeter of the body, wherein the suture engagement slot is configured to receive a suture laterally through the inlet and has a narrow, tortuous portion configured to apply a pinching force to the suture such that the device secures to the suture and resists the suture from moving axially through the device along a longitudinal axis of the suture;
a locking tab that has an open position wherein the suture engagement slot is permitted to widen such that a suture can enter laterally through the inlet into the narrow, tortuous portion of the suture engagement slot, and the locking tab has a closed position wherein the suture engagement slot is retained against widening and the inlet is blocked; and
a first hole passing through the body and a second hole passing through the body, the first and second holes being positioned on opposing sides of the suture engagement slot and spaced apart laterally from the suture engagement slot, wherein the first and second holes are configured to receive a tool that applies a separation force to the suture engagement slot.

15. The device of claim 14, wherein the locking tab has two or more different closed positions that each correspond a different maximum width of the suture engagement slot.

16. The device of claim 14, wherein the locking tab forms a ratcheting mechanism to allow the locking tab to move from a first closed position to a second closed position by applying a compression force on the device, wherein the suture engagement slot has a smaller width in the second closed position compared to the first closed position.

17. The device of claim 14, further comprising a second locking tab.

18. The device of claim 14, wherein the locking tab is resiliently deformed in the open position and is biased toward the closed position.

19. The device of claim 14, further comprising a second suture engagement slot in the body, and wherein the locking tab retains the second suture engagement slot against widening when the locking tab is in the closed position.

20. The device of claim 14, wherein the narrow, tortuous portions comprises at least three alternating apices.

\* \* \* \* \*